United States Patent [19]

Krenzer

[11] 4,007,031
[45] Feb. 8, 1977

[54] 2-ALKYL-4-THIADIAZOLYL-1,2,4-TRIAZOLIDIN-3-ONES

[75] Inventor: John Krenzer, Oak Park, Ill.

[73] Assignee: Velsicol Chemical Corporation, Chicago, Ill.

[22] Filed: Sept. 18, 1975

[21] Appl. No.: 614,464

Related U.S. Application Data

[62] Division of Ser. No. 455,697, March 28, 1974, Pat. No. 3,931,209.

[52] U.S. Cl. .................................................. 71/90
[51] Int. Cl.² ......................................... A01N 9/12
[58] Field of Search ........................................ 71/90

[56] References Cited
UNITED STATES PATENTS

| | | | |
|---|---|---|---|
| 3,734,923 | 5/1973 | Dowding et al. | 71/90 X |
| 3,759,939 | 9/1973 | Metzger et al. | 71/90 X |
| 3,849,432 | 11/1974 | Metzger et al. | 71/90 X |
| 3,929,816 | 12/1975 | Rathgeb et al. | 71/90 X |

Primary Examiner—Joseph Paul Brust
Attorney, Agent, or Firm—Robert J. Schwarz; Dietmar H. Olesch

[57] ABSTRACT

This invention discloses compounds of the formula

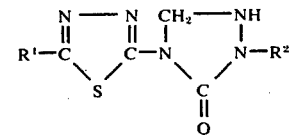

wherein R¹ is selected from the group consisting of alkyl, alkenyl, chloroalkyl, trifluoromethyl, alkoxy, alkylthio, alkylsulfonyl, alkylsulfinyl and cycloalkyl of from 3 to 7 carbon atoms optionally substituted with from 1 to 2 substituents selected from the group consisting of alkyl, alkoxy and halogen; and R² is alkyl. Further disclosed are herbicidal compositions containing a compound of the above description.

9 Claims, No Drawings

2-ALKYL-4-THIADIAZOLYL-1,2,4-TRIAZOLIDIN-3-ONES

This application is a division of copending application Ser. No. 455,697, filed Mar. 28, 1974, now U.S. Pat. No. 3,931,209, issued Jan. 6, 1976.

This invention relates to new compositions of matter and more specifically relates to new chemical compounds of the formula

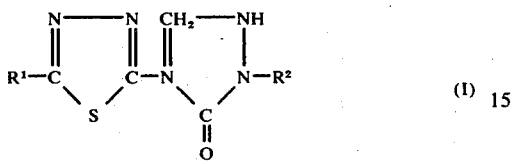

wherein $R^1$ is selected from the group consisting of alkyl, alkenyl, chloroalkyl, trifluoromethyl, alkoxy, alkylthio, alkylsulfonyl, alkylsulfinyl and cycloalkyl of from 3 to 7 carbon atoms optionally substituted with from 1 to 2 substituents selected from the group consisting of alkyl, alkoxy and halogen; and $R^2$ is alkyl.

The compounds of this invention are unexpectedly useful as herbicides.

In a preferred embodiment of the present invention $R^1$ is selected from the group consisting of lower alkyl, lower alkenyl, lower chloroalkyl, trifluoromethyl, lower alkoxy, lower alkylthio, lower alkylsulfonyl, lower alkylsulfinyl and cycloalkyl of from 3 to 7 carbon atoms optionally substituted with from 1 to 2 substituents selected from the group consisting of lower alkyl, lower alkoxy, chlorine, bromine and fluorine.

The term lower as used herein designates a straight or branched carbon chain of up to six carbon atoms.

The compounds of this invention can be prepared by reacting a semicarbazide of the formula

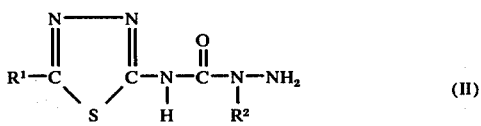

wherein $R^1$ and $R^2$ are as heretofore defined, with formaldehyde. This reaction can be effected by combining a solution of a molar amount of the semicarbazide of formula II in a water miscible solvent such as methanol with an about equimolar or slight excess molar amount of aqueous formaldehyde. Inorganic base such as potassium hydroxide can be added to raise the pH of the reaction medium to from about 7 to about 9. The reaction can be carried out at room temperature or at slightly elevated temperatures such as temperatures ranging up to about 50° C. The reaction mixture can then be stirred or allowed to stand for a period of up to about 8 hours to ensure completion of the reaction. The product can then be recovered as a precipitate by filtration and can be dried. This product can then be used as such or can be further purified by conventional means such as recrystallization, washing and the like.

The semicarbazide of formula II can be prepared by reacting a molar amount of an isocyanate dimer of the formula

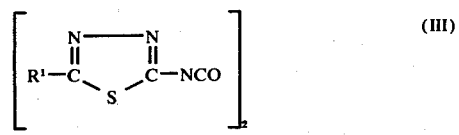

wherein $R^1$ is as heretofore described, with at least about two molar amounts of a hydrazine of the formula

wherein $R^2$ is as heretofore described. This reaction can be effected by adding the isocyanate dimer of formula III to a solution of the hydrazine of formula IV in an inert organic solvent such as methylene chloride at room temperature with stirring. After the addition is completed the reaction mixture can be heated at temperatures of up to the reflux temperature of the mixture for a period of up to about 2 hours. After this time the mixture can be stripped of solvent and excess hydrazine by vacuum distillation to yield the desired product.

The isocyanate dimer of formula III can be prepared by reacting a thiadiazole of the formula

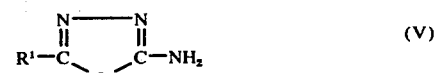

wherein $R^1$ is as heretofore described, with phosgene. This reaction can be effected by adding a slurry or solution of the thiadiazole, in a suitable organic solvent such as ethyl acetate, to a saturated solution of phosgene in an organic solvent such as ethyl acetate. The resulting mixture can be stirred at ambient temperatures for a period of from about 4 to about 24 hours. The reaction mixture can then be purged with nitrogen gas to remove unreacted phosgene. The desired product can then be recovered by filtration if formed as a precipitate or upon evaporation of the organic solvent used if soluble therein. This product can be used as such or can be further purified if desired.

Exemplary thiadiazoles of formula V useful for preparing the compounds of the present invention are 5-methyl-2-amino-1,3,4-thiadiazole, 5-ethyl-2-amino-1,3,4-thiadiazole, 5-propyl-2-amino-1,3,4-thiadiazole, 5-allyl-2-amino-1,3,4-thiadiazole, 5-pent-3-enyl-2-amino-1,3,4-thiadiazole, 5-chloromethyl-2-amino-1,3,4-thiadiazole, 5β-chloroethyl-2-amino-1,3,4-thiadiazole, 5-γ-chloropropyl-2-amino-1,3,4-thiadiazole, 5-trichloromethyl-2-amino-1,3,4-thiadiazole, 5-methoxy-2-amino-1,3,4-thiadiazole, 5-ethoxy-2-amino-1,3,4-thiadiazole, 5-propoxy-2-amino-1,3,4-thiadiazole, 5-butyloxy-2-amino-1,3,4-thiadiazole, 5-hexyloxy-2-amino-1,3,4-thiadiazole, 5-methylthio-2-amino-1,3,4-thiadiazole, 5-ethylthio-2-amino-1,3,4-thiadiazole, 5-propylthio-2-amino-1,3,4-thiadiazole, 5-butylthio-2-amino-1,3,4-thiadiazole, 5-methylsulfonyl-2-amino-1,3,4-thiadiazole, 5-ethylsulfonyl-2-amino-1,3,4-thiadiazole, 5-butylsulfonyl-2-amino-1,3,4-thiadiazole, 5-methylsulfinyl-2-amino-1,3,4-thiadiazole, 5-ethylsulfinyl-2-amino-1,3,4-thiadiazole, 5-propylsulfinyl-2-amino-1,3,4- thiadiazole, 5-t-butyl-2-amino-1,3,4-thiadiazole, 5-trifluoromethyl-2-amino-1,3,4-thiadiazole, 5-cyclopropyl-2-amino-1,3,4-thiadiazole, 5-cyclobutyl-2-amino-1,3,4-thiadiazole, 5-cyclopentyl-2-amino-1,3,4-thiadiazole, 5-cyclohexyl-2-amino-1,3,4-thiadiazole, 5-cycloheptyl-2-amino-1,3,4-thiadiazole, 5-(2-methylcyclopropyl)-2-amino-1,3,4-thiadiazole, 5-(3-ethylcyclopentyl)-2-amino-1,3,4-thiadiazole, 5-(4-propylcyclohexyl)-2-amino-1,3,4-thiadiazole, 5-(4-chlorocyclohexyl)-2-amino-1,3,4-thiadiazole, 5-(4-bromocyclohexyl)-2-amino-1,3,4-thiadiazole, 5-(4-fluorocyclohexyl)-2-amino-1,3,4-thiadiazole, 5-(3-methoxycycloheptyl)-2-amino-1,3,4-thiadiazole, 5-(3-hexylcyclopentyl)-2-amino-1,3,4-thiadiazole, 5-(4-hexyloxycyclohexyl)-2-amino-1,3,4-thiadiazole, 5-(4-iodocyclohexyl)-2-amino-1,3,4-thiadiazole and the like.

Exemplary suitable hydrazines of formula IV for preparing the compounds of the present invention are methylhydrazine, ethylhydrazine, n-propylhydrazine, isopropylhydrazine, n-butylhydrazine, sec-butylhydrazine, t-butylhydrazine, pentylhydrazine and hexylhydrazine.

The manner in which the compounds of this invention can be prepared is more specifically illustrated in the following examples.

EXAMPLE 1

Preparation of 5-Trifluoromethyl-1,3,4-thiadiazol-2-yl Isocyanate Dimer

A saturated solution of phosgene in ethyl acetate (100 ml) was charged into a glass reaction vessel equipped with a mechanical stirrer. A slurry of 5-trifluoromethyl-2-amino-1,3,4-thiadiazole (45 grams) in ethyl acetate (300 ml) was added to the reaction vessel and the resulting mixture was stirred for a period of about 16 hours resulting in the formation of a precipitate. The reaction mixture was then purged with nitrogen gas to remove unreacted phosgene. The purged mixture was filtered to recover 48 grams of a white solid. This solid was recrystallized from dimethyl formamide to yield the desired product 5-trifluoromethyl-1,3,4-thiadiazol-2-yl isocyanate dimer.

EXAMPLE 2

Preparation of 2-Methyl-4-(5-trifluoromethyl-1,3,4-thiadiazol-2-yl)semicarbazide A solution of methylhydrazine (6.5 grams) in methylene chloride (100 ml) was charged into a glass reaction vessel equipped with a mechanical stirrer, thermometer and reflux condenser. 5-Trifluoromethyl-1,3,4-thiadiazol-2-yl isocyanate dimer (25 grams) was then added, with stirring at a temperature of from 20° to 25° C. Additional methylhydrazine (3.0 grams) was then added and the reaction mixture was heated at reflux for a period of about 4 hours. After this time the reaction mixture was stripped of solvent and excess hydrazine to yield the desired product 2-methyl-4-(5-trifluoromethyl-1,3,4-thiadiazol-2-yl) semicarbazide as a residual oil.

EXAMPLE 3

Preparation of 2-Methyl-4-(5-trifluoromethyl-1,3,4-thiadiazol-2-yl)-1,2,4-triazolidin-3-one The 2-methyl-4-(5-trifluoromethyl-1,3,4-thiadiazol-2-yl)semicarbazide prepared in Example 2 was dissolved in methanol (100 ml) in a glass reaction flask equipped with a mechanical stirrer and thermometer. Aqueous formaldehyde (12 ml; 37% concentration) was then added to the flask with stirring. The reaction mixture warmed to a temperature of about 35° C. Sufficient aqueous potassium hydroxide was then added to adjust the pH of the reaction medium to from about 7 to 8. A solid precipitate was formed. The precipitate was then recovered by filtration, was recrystallized from an ethyl acetate-heptane mixture and was dried under vacuum to yield the desired product 2-methyl-4-(5-trifluoromethyl-1,3,4-thiadiazol-2-yl)-1,2,4-triazolidin-3-one having a melting point of 187° to 188° C.

EXAMPLE 4

Preparation of 5-t-Butyl-1,3,4-thiadiazol-2-yl Isocyanate Dimer

A saturated solution of phosgene in ethyl acetate (100 ml) was charged into a glass reaction vessel equipped with a mechanical stirrer. A slurry of 5-t-butyl-2-amino-1,3,4-thiadiazole (10 grams) in ethyl acetate (300 ml) was added to the reaction vessel and the resulting mixture was stirred for a period of about 16 hours resulting in the formation of a precipitate. The reaction mixture was then purged with nitrogen gas to remove unreacted phosgene. The purged mixture was then filtered to recover the desired product 5-t-butyl-1,3,4-thiadiazol-2-yl isocyanate dimer as a solid having a melting point of 261° to 263° C.

EXAMPLE 5

Preparation of 2-Methyl-4-(5-t-butyl-1,3,4-thiadiazol-2-yl)semicarbazide

A solution of methylhydrazine (0.3 mole) in methylene chloride (150 ml) is charged into a glass reaction vessel equipped with a mechanical stirrer, thermometer and reflux condenser. 5-t-Butyl-1,3,4-thiadiazol-2-yl isocyanate dimer (0.1 mole) is then added, with stirring, at room temperature. After the addition is completed the reaction mixture is heated at reflux for a period of about 4 hours. After this time the reaction mixture is stripped of solvent and excess hydrazine to yield the desired product 2-methyl-4-(5-t-butyl-1,3,4-thiadiazol-2-yl)semicarbazide as the residue.

EXAMPLE 6

Preparation of 2-Methyl-4-(5t-butyl-1,3,4-thiadiazol-2-yl)-1,2,4-triazolidin-3-one 2-Methyl-4-(5-t-butyl-1,3,4-thiadiazol-2-yl)-semicarbazide (0.1 mole) dissolved in methanol (100 ml) is charged into a glass reaction vessel equipped with a mechanical stirrer and thermometer. Aqueous formaldehyde (0.2 mole; 37% concentration) is then added to the reaction vessel with stirring. Dilute aqueous potassium hydroxide is added to the reaction mixture to adjust the pH to between 7 and 8 and stirring is continued for a period of about 20 minutes resulting in the formation of a solid precipitate. The precipitate is recovered by filtration, is recrystallized and is dried under vacuum to yield the desired product 2-methyl-4-(5-t-butyl-1,3,4-thiadiazol-2-yl)-1,2,4-triazolidin-3-one.

EXAMPLE 7

Preparation of 5-Methyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methyl-2-amino-1,3,4-thiadiazole (40 grams) in ethyl acetate (300ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methyl-1,3,4-thiadiazol-2-yl isocyanate dimer.

EXAMPLE 8

Preparation of 2-Ethyl-4-(5-methyl-1,3,4-thiadiazol-2-yl)semicarbazide

A solution of ethylhydrazine (0.3 mole) in methylene chloride (150 ml) is charged into a glass reaction vessel equipped with a mechanical stirrer, thermometer and reflux condenser. 5-Methyl-1,3,4-thiadiazol-2-yl isocyanate dimer (0.1 mole) is then added, with stirring, at room temperature. After the addition is completed the reaction mixture is heated at reflux for a period of about 4 hours. After this time the reaction mixture is stripped of solvent and excess hydrazine to yield the desired product 2-ethyl-4-(5-methyl-1,3,4-thiadiazol-2-yl)semicarbazide as the residue.

EXAMPLE 9

Preparation of 2-Ethyl-4-(5-methyl-1,3,4-thiadiazol-2-yl)-1,2,4-triazolidin-3-one 2-Ethyl-4-(5-methyl-1,3,4-thiadiazol-2-yl)semicarbazide (0.1 mole) dissolved in methanol (100 ml) is charged into a glass reaction vessel equipped with a mechanical stirrer and thermometer. Aqueous formaldehyde (0.2 mole; 37% concentration) is then added to the reaction vessel with stirring. Dilute aqueous potassium hydroxide is added to the reaction mixture to adjust the pH to between 7 and 8 and stirring is continued for a period of about 20 minutes resulting in the formation of a solid precipitate. The precipitate is recovered by filtration, is recrystallized and is dried under vacuum to yield the desired product 2-ethyl-4-(5-methyl-1,3,4-thiadiazol-2-yl)-1,2,4-triazolidin-3-one.

EXAMPLE 10

Preparation of 5-Methoxy-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methoxy-2-amino-1,3,4-thiadiazole (40 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methoxy-1,3,4-thiadiazol-2-yl isocyanate dimer.

EXAMPLE 11

Preparation of 2-Propyl-4-(5-methoxy-1,3,4-thiadiazol-2-yl)semicarbazide

A solution of propylhydrazine (0.3 mole) in methylene chloride (150 ml) is charged into a glass reaction vessel equipped with a mechanical stirrer, thermometer and reflux condenser. 5-Methoxy-1,3,4-thiadiazol-2-yl isocyanate dimer (0.1 mole) is then added, with stirring, at room temperature. After the addition is completed the reaction mixture is heated at reflux for a period of about 4 hours. After this time the reaction mixture is stripped of solvent and excess hydrazine to yield the desired product 2-propyl-4-(5-methoxy-1,3,4-thiadiazol-2-yl)semicarbazide as the residue.

EXAMPLE 12

Preparation of 2-Propyl-4-(5-methoxy-1,3,4-thiadiazol-2-yl)-1,2,4-triazolidin-3-one 2-Propyl-4-(5-methoxy-1,3,4-thiadiazol-2-yl)-semicarbazide (0.1 mole) dissolved in methanol (100 ml) is charged into a glass reaction vessel equipped with a mechanical stirrer and thermometer. Aqueous formaldehyde (0.2 mole; 37% concentration) is then added to the reaction vessel with stirring. Dilute aqueous potassium hydroxide is added to the reaction mixture to adjust the pH to between 7 and 8 and stirring is continued for a period of about 20 minutes resulting in the formation of a solid precipitate. The precipitate is recovered by filtration, is recrystallized and is dried under vacuum to yield the desired product 2-propyl-4-(5-methoxy-1,3,4-thiadiazol-2-yl)-1,2,4-triazolidin-3-one.

EXAMPLE 13

Preparation of 5-Methylthio-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methylthio-2-amino-1,3,4-thiadiazole (45 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methylthio-1,3,4-thiadiazol-2-yl isocyanate dimer.

EXAMPLE 14

Preparation of 2-Methyl-4-(5-methylthio-1,3,4-thiadiazol-2-yl)semicarbazide

A solution of methylhydrazine (0.3 mole) in methylene chloride (150 ml) is charged into a glass reaction vessel equipped with a mechanical stirrer, thermometer and reflux condenser. 5-Methylthio-1,3,4-thiadiazol- 2-yl isocyanate dimer (0.1 mole) is then added, with stirring, at room tempertaure. After the addition is completed the reaction mixture is heated at reflux for a period of about 4 hours. After this time the reaction mixture is stripped of solvent and excess hydrazine to yield the desired product 2-methyl-4-(5-methylthio-1,3,4-thiadiazol-2-yl) semicarbazide as the residue.

EXAMPLE 15

Preparation of 2-Methyl-4-(5-methylthio-1,3,4-thiadiazol-2-yl)-1,2,4-triazolidin-3-one 2-Methyl-4-(5-methylthio-1,3,4-thiadiazol-2-yl)-semicarbazide (0.1 mole) dissolved in methanol (100 ml) is charged into a glass reaction vessel equipped with a mechanical stirrer and thermometer. Aqueous formaldehyde (0.2 mole; 37% concentration) is then added to the reaction vessel with stirring. Dilute aqueous potassium hydroxide is added to the reaction mixture to adjust the pH to between 7 and 8 and stirring is continued for a period of about 20 minutes resulting in the formation of a solid precipitate. The precipitate is recovered by filtration, is recrystallized and is dried under vacuum to yield the desired product 2-methyl-4-(5-methylthio-1,3,4-thiadiazol-2-yl)-1,2,4-triazolidin-3-one.

EXAMPLE 16

Preparation of 5-Methylsulfonyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methylsulfonyl-2-amino-1,3,4-thiadiazole (50 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methylsulfonyl-1,3,4-thiadiazol-2-yl isocyanate dimer.

EXAMPLE 17

Preparation of 2-n-Butyl-4-(5-methylsulfonyl-1,3,4-thiadiazol-2-yl)semicarbazide A solution of n-butylhydrazine (0.3 mole) in methylene chloride (150 ml) is charged into a glass reaction vessel equipped with a mechanical stirrer, thermometer and reflux condenser. 5-Methylsulfonyl-1,3,4-thiadiazol-2-yl isocyanate dimer (0.1 mole) is then added, with stirring, at room temperature. After the addition is completed the reaction mixture is heated at reflux for a period of about 4 hours. After this time the reaction mixture is stripped of solvent and excess hydrazine to yield the desired product 2-n-butyl-4-(5-methylsulfonyl-1,3,4-thiadiazol-2-yl)semicarbazide as the residue.

EXAMPLE 18

Preparation of 2-n-Butyl-4-(5-methylsulfonyl-1,3,4-thiadiazol-2-yl)-1,2,4-triazolidin-3-one 2-n-Butyl-4-(5-methylsulfonyl-1,3,4-thiadiazol-2-yl)-semicarbazide (0.1 mole) dissolved in methanol (100 ml) is charged into a glass reaction vessel equipped with a mechanical stirrer and thermometer. Aqueous formaldehyde (0.2 mole; 37% concentration) is then added to the reaction vessel with stirring. Dilute aqueous potassium hydroxide is added to the reaction mixture to adjust the pH to between 7 to 8 and stirring is continued for a period of about 20 minutes resulting in the formation of a solid precipitate. The precipitate is recovered by filtration, is recrystallized and is dried under vacuum to yield the desired product 2-n-butyl-4-(5-methylsulfonyl-1,3,4-thiadiazol-2-yl)-1,2,4-triazolidin-3-one.

EXAMPLE 19

Preparation of 5-Methylsulfinyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-methylsulfinyl-2-amino-1,3,4-thiadiazole (50 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-methylsulfinyl-1,3,4-thiadiazol-2-yl isocyanate dimer.

EXAMPLE 20

Preparation of 2-n-Hexyl-4-(5-methylsulfinyl-1,3,4-thiadiazol-2-yl)semicarbazide A solution of n-hexylhydrazine (0.3 mole) in methylene chloride (150 ml) is charged into a glass reaction vessel equipped with a mechanical stirrer, thermometer and reflux condenser. 5-Methylsulfinyl-1,3,4-thiadiazol-2-yl isocyanate dimer (0.1 mole) is then added, with stirring, at room temperature. After the addition is completed the reaction mixture is heated at reflux for a period of about 4 hours. After this time the reaction mixture is stripped of solvent and excess hydrazine to yield the desired product 2-n-hexyl-4-(5-methylsulfinyl-1,3,4-thiadiazol-2-yl)semicarbazide as the residue.

EXAMPLE 21

Preparation of 2-n-Hexyl-4-(5-methylsulfinyl-1,3,4-thiadiazol-2-yl)-1,2,4-triazolidin-3-one 2-n-Hexyl-4-(5-methylsulfinyl-1,3,4-thiadiazol-2-yl)-semicarbazide (0.1 mole) dissolved in methanol (100 ml) is charged into a glass reaction vessel equipped with a mechanical stirrer and thermometer. Aqueous formaldehyde (0.2 mole; 37% concentration) is then added to the reaction vessel with stirring. Dilute aqueous potassium hydroxide is added to the reaction mixture to adjust the pH to between 7 and 8 and stirring is continued for a period of about 20 minutes resulting in the formation of a solid precipitate. The precipitate is recovered by filtration, is recrystallized and is dried under vacuum to yield the desired product 2-n-hexyl-4-(5-methylsulfinyl-1,3,4-thiadiazol-2-yl)-1,2,4-triazolidin-3-one.

EXAMPLE 22

Preparation of 5-Cyclobutyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-cyclobutyl-2-amino-1,3,4-thiadiazole (50 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-cyclobutyl-1,3,4-thiadiazol-2-yl isocyanate dimer.

EXAMPLE 23

Preparation of 2-Methyl-4-(5-cyclobutyl-1,3,4-thiadiazol-2-yl)semicarbazide

A solution of methylhydrazine (0.3 mole) in methylene chloride (150 ml) is charged into a glass reaction vessel equipped with a mechanical stirrer, thermometer and reflux condenser. 5-cyclobutyl-1,3,4-thiadrazol-2-yl isocyanate dimer (0.1 mole) is then added, with stirring, at room temperature. After the addition is completed the reaction mixture is heated at reflux for a period of about 4 hours. After this time the reaction mixture is stripped of solvent and excess hydrazine to yield the desired product 2-methyl-4-(5-cyclobutyl-1,3,4-thiadiazol-2-yl)semicarbazide.

EXAMPLE 24

Preparation of 2-Methyl-4-(5-cyclobutyl-1,3,4-thiadiazol-2-yl)-1,2,4-triazolidin-3-one 2-Methyl-4-(5-cyclobutyl-1,3,4-thiadiazol-2-yl)-semicarbazide (0.1 mole) dissolved in methanol (100 ml) is charged into a glass reaction vessel equipped with a mechanical stirrer and thermometer. Aqueous formaldehyde (0.2 mole; 37% concentration) is then added to the reaction vessel with stirring. Dilute aqueous potassium hydroxide is added to the reaction mixture to adjust the pH to between 7 and 8 and stirring is continued for a period of about 20 minutes resulting in the formation of a solid precipitate. The precipitate is recovered by filtration, is recrystallized and is dried under vacuum to yield the desired product 2-methyl-4-(5-cyclobutyl-1,3,4-thiadiazol-2-yl)-1,2,4-triazolidin-3-one.

EXAMPLE 25

Preparation of 5-Cyclohexyl-1,3,4-thiadiazol-2-yl Isocyanate Dimer

A saturated solution of phosgene in ethyl acetate (100 ml) is charged into a glass reaction vessel equipped with a mechanical stirrer. A slurry of 5-cyclohexyl-2-amino-1,3,4-thiadiazole (50 grams) in ethyl acetate (300 ml) is added to the reaction vessel and the resulting mixture is stirred for a period of about 16 hours, resulting in the formation of a precipitate. The reaction mixture is then purged with nitrogen gas to remove unreacted phosgene. The purged mixture is then filtered to recover the precipitate. The precipitate is then recrystallized to yield the desired product 5-cyclohexyl-1,3,4-thiadiazol-2-yl isocyanate dimer.

EXAMPLE 26

Preparation of 2-Methyl-4-(5-cyclohexyl-1,3,4-thiadiazol-2-yl)semicarbazide

A solution of methylhydrazine (0.3 mole) in methylene chloride (150 ml) is charged into a glass reaction vessel equipped with a mechanical stirrer, thermometer and reflux condenser. 5-cyclohexyl-1,3,4-thiadiazol-2-yl isocyanate dimer (0.1 mole) is then added, with stirring, at room temperature. After the addition is completed the reaction mixture is heated at reflux for a period of about 4 hours. After this time the reaction mixture is stripped of solvent and excess hydrazine to yield the desired product 2-methyl-4-(5-cyclohexyl-1,3,4-thiadiazol-2-yl)semicarbazide as the residue.

EXAMPLE 27

Preparation of 2-Methyl-4-(5-cyclohexyl-1,3,4-thiadiazol-2-yl)-1,2,4-triazolidin-3-one 2-Methyl-4-(5-cyclohexyl-1,3,4-thiadiazol-2-yl)-semicarbazide (0.1 mole) dissolved in methanol (100 ml) is charged into a glass reaction vessel equipped with a mechanical stirrer and thermometer. Aqueous formaldehyde (0.2 mole; 37% concentration) is then added to the reaction vessel with stirring. Dilute aqueous potassium hydroxide is added to the reaction mixture to adjust the pH to between 7 and 8 and stirring is continued for a period of about 20 minutes resulting in the formation of a solid precipitate. The precipitate is recovered by filtration, is recrystallized and is dried under vacuum to yield the desired product 2-methyl-4-(5-cyclohexyl-1,3,4-thiadiazol-2-yl)-1,2,4-triazolidin-3-one.

Additional exemplary compounds within the scope of the present invention which can be prepared by the procedures of the foregoing examples are 2-methyl-4-(5-ethyl-1,3,4-thiadiazol-2yl)-1,2,4-triazolidin-3-one, 2-methyl-4-(5-isopropyl-1,3,4-thiadiazol-2-yl)-1,2,4-triazolidin-3-one, 2-methyl-4-(5-hexyl-1,3,4-thiadiazol-2-yl)-1,2,4-triazolidin-3-one, 2-methyl-4-(5-ethoxy-1,3,4-thiadiazol-2yl)-1,2,4-triazolidin-3one, 2-methyl-4-(5-butoxy-1,3,4-thiadiazol-2-yl)-1,2,4-triazolidin-3-one, 2-methyl-4-(5-hexyloxy-1,3,4-thiadiazol-2-yl)-1,2,4-triazolidin-3-one, 2-methyl-4-(5-ethylthio-1,3,4-thiadiazol-2-yl)-1,2,4-triazolidin-3-one, 2-methyl-4-(5-propylthio-1,3,4-thiadiazol-2-yl)-1,2,4-triazolidin-3-one, 2-methyl-4-(5-hexylthio-1,3,4-thiadiazol-2-yl)-1,2,4-triazolidin-3-one, 2-methyl-4-(5-allyl-1,3,4-thiadiazol-2-yl)-1,2,4-triazolidin-3-one, 2-methyl-4-(5-pent-3-enyl-1,3,4-thiadiazol-2-yl)-1,2,4-triazolidin-3-one, 2-methyl-4-(5-hex-3-enyl-1,3,4-thiadiazol-2-yl)-1,2,4-triazolidin-3-one, 2-methyl-4-(5-chloromethyl-1,3,4-thiadiazol-2-yl)-1,2,4-triazolidin-3-one, 2-methyl-4-(5-β-chloroethyl-1,3,4-thiadiazol-2-yl)-1,2,4-triazolidin-3-one, 2-methyl-4-(5-γ-chloropropyl-1,3,4-thiadiazol-2-yl)-1,2,4-triazolidin-3-one, 2-methyl-4-(5-ethylsulfonyl-1,3,4-thiadiazol-2-yl)-1,2,4-triazolidin-3-one, 2-methyl-4-(5-propylsulfonyl-1,3,4-thiadiazol-2-yl)-1,2,4-triazolidin-3-one, 2-methyl-4-(5-hexylsulfonyl-1,3,4-thiadiazol-2-yl)-1,2,4-triazolidin-3-one, 2-methyl-4-(5-ethylsulfinyl-1,3,4-thiadiazol-2-yl)-1,2,4-triazolidin-3-one, 2-methyl-4-(5-butylsulfinyl-1,3,4-thiadiazol-2-yl)-1,2,4-triazolidin-3-one, 2- methyl-4-(5-cyclopropyl-1,3,4-thiadiazol-2-yl)-1,2,4-triazolidin-3-one, 2-methyl-4-(5-cyclopentyl-1,3,4-thiadiazol-2-yl)-1,2,4-triazolidin-3-one, 2-methyl-4-(5-cyclohexyl-1,3,4-thiadiazol-2-yl)-1,2,4-triazolidin-3-one, 2-methyl-4-[5-(3-methylcyclohexyl)-1,3,4-thiadiazol-2-yl]-1,2,4-triazolidin-3-one, 2-methyl-4-[5-(3-ethylcyclohexyl)-1,3,4-thiadiazol-2-yl]-1,2,4-triazolidin-3-one, 2-methyl-4-[5-(3-propylcyclohexyl)-1,3,4-thiadiazol-2-yl]-1,2,4-triazolidin-3-one, 2-methyl-4-[5-(4-chlorocyclohexyl)-1,3,4-thiadiazol-2-yl]-1,2,4-triazolidin-3-one, 2-methyl-4-[5-(4-bromocyclohexyl)-1,3,4-thiadiazol-2-yl]-1,2,4-triazolidin-3-one, 2-methyl-4-[5-(4-fluorocyclohexyl)-1,3,4-thiadiazol-2-yl]-1,2,4-triazolidin-3-one, 2-methyl-4-[5-(2-methoxycyclohexyl)-1,3,4-thiadiazol-2-yl]-1,2,4-triazolidin-3-one, 2-methyl-4-[5-(3-ethoxycyclohexyl)-1,3,4-thiadiazol-2-yl]-1,2,4-triazolidin-3-one, 2-methyl-4-[5-(4-hexyloxycyclohexyl)-1,3,4-thiadiazol-2-yl]-1,2,4-triazolidin-3-one and 2-methyl-4-[5-(3,4-dichlorocyclohexyl)-1,3,4-thiadiazol-2-yl]-1,2,4-triazolidin-3-one.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols, or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 28

| Preparation of a Dust | |
|---|---|
| Product of Example 3 | 10 |
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists, and the like.

The compounds of the present invention are also useful when combined with other herbicides and/or defoliants, dessicants, growth inhibitors, and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, alachlor, 4(2,4-DB), 2,4-DEB, 4-CPB, 4-CPA, 4-CPP, 2,4,5-TB, 2,4,5TES, 3,4-DA, silvex and the like; carbamate herbicides such as IPC, CIPC, swep, barban, BCPC, CEPC, CPPC, and the like; thiocarbamate and dithiocarbamate herbicides such as CDEC, metham sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine herbicides such as simazine, chlorazine, atraone, desmetryne, norazine, ipazine, prometryn, ataone, trietazine, simetone, prometone, propazine, ametryne and the like; chloroacetamide herbicides such as alpha-chloro-N,N-dimethylacetamide, CDEA, CDAA, alpha-chloro-N-isopropylacetamide, 2-chloro-N-isopropyl-acetanilide, 4-(chloroacetyl)morpholine, 1-

(chloroacetyl)-piperidine, and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, tricamba, amiben, fenac, PBA, 2-methoxy-3,6-dichlorophenylacetic acid, 3-methoxy-2,6-dichlorophenylacetic acid, 2-methoxy-3,5,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2901, planavin, sodium tetraborate, calcium cyanamid, DEF, ethyl xanthogen disulfide, sindone, sindone B, propanil and the like.

Such herbicides can also be used in the methods and compositions of this invention in the form of their salts, esters, amides, and other derivatives whenever applicable to the particular parent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarters, foxtail, crabgrass, wild mustard, field pennycress, ryegrass, goose-grass, chickweed, wild oats, velvetleaf, purslane, barnyard grass, smartweed, knotweed, cocklebur, wild buckwheat, kochia, medic, corn cockle, ragweed, sowthistle, coffeeweed, croton, cuphea, dodder, fumitory, groundsel, hemp nettle, knawel, spurge, spurry, emex, jungle rice, pondweed, dog fennel, carpetweed, morning glory, bedstraw, ducksalad, naiad, cheatgrass, fall panicum, jimsonweed, witchgrass, switchgrass, watergrass, teaweed, wild turnip and sprangletop; biennials such as wild carrot, matricaria, wild barley, campion, chamomile, burdock, mullein, roundleaved mallow, bull thistle, hounds-tongue, moth mullein and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail, wintercress, horsenettle, nutsedge, milkweed and sicklepod.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively non-toxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of an active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after seeding the pots were sprayed with water until the soil was wet and the compound 2-methyl-4-(5-trifluoromethyl-1,3,4-thiadiazol-2-yl)-1,2,4-triazolidin-3-one formulated as an aqueous emulsion of an acetone solution containing emulsifiers was sprayed at a concentration of 10 pounds per acre on the surface of the soil.

After spraying, the soil containers were placed in the greenhouse and provided with supplementary heat as required and daily or more frequent watering. The plants were maintained under these conditions for a period of from 15 to 21 days, at which time the condition of the plants and the degree of injury to the plants was rated on a scale of from 0 to 10, as follows: 0 = no injury, 1,2 = slight injury, 3,4 = moderate injury, 5,6 = moderately severe injury, 7,8,9 = severe injury and 10 = death. The effectiveness of this compound is demonstrated by the following table.

The herbicidal activity of the compounds of this invention was also demonstrated by experiments carried out for the post-emergence control of a variety of weeds. In these experiments the compound 2-methyl-4-(5-trifluoromethyl-1,3,4-thiadiazol-2-yl)-1,2,4-triazolidin-3-one was formulated as an aqueous emulsion and sprayed at 10 pounds per acre on the foliage of the weeds that have attained a prescribed size. After spraying the plants were placed in a greenhouse and watered daily or more frequently. Water was not applied to the foliage of the treated plants. The severity of the injury was determined 10 to 15 days after treatment and was rated on the scale of from 0 to 10 heretofore described. The effectiveness of this compound is demonstrated by the data in the following table.

INJURY RATING

| Weed Species | Product of Example 3 at 10 lbs/acre | |
|---|---|---|
| | Pre-emergence | Post-emergence |
| Yellow Nutsedge | 0 | 0 |
| Wild Oats | 7 | 3 |
| Jimsonweed | 10 | 10 |
| Velvetleaf | 10 | 10 |
| Johnsongrass | 8 | 3 |
| Pigweed | 9 | 7 |
| Mustard | 10 | 10 |
| Yellow Foxtail | 9 | 2 |
| Barnyardgrass | 8 | 3 |
| Crabgrass | 8 | 6 |
| Cheatgrass | 7 | — |
| Morningglory | 5 | 8 |

I claim:

1. A herbicidal composition comprising an inert carrier and, as an essential active ingredient, in a quantity toxic to weeds, a compound of the formula

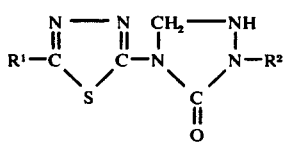

wherein $R^1$ is selected from the group consisting of lower alkyl, lower alkenyl, lower chloroalkyl, trifluoromethyl, lower alkoxy, lower alkylthio, lower alkylsulfonyl, lower alkylsulfinyl, and cycloalkyl of from 3 to 7 carbon atoms optionally substituted with from 1 to 2 substituents selected from the group consisting of lower alkyl, lower alkoxy, chlorine, bromine, and fluorine; and $R^2$ is lower alkyl.

2. The herbicidal composition of claim 1 wherein the compound is 2-methyl-4-(5-trifluoromethyl-1,3,4-thiadiazol-2-yl)-1,2,4-triazolidin-3-one.

3. The herbicidal composition of claim 1 wherein the compound is 2-methyl-4-(5-t-butyl-1,3,4-thiadiazol-2-yl)-1,2,4-triazolidin-3-one.

4. The herbicidal composition of claim 1 wherein the compound is 2-ethyl-4-(5-methyl-1,3,4-thiadiazol-2-yl)-1,2,4-triazolidin-3-one.

5. The herbicidal composition of claim 1 wherein the compound is 2-propyl-4-(5-methoxy-1,3,4-thiadiazol-2-yl)-1,2,4-triazolidin-3-one.

6. The herbicidal composition of claim 1 wherein the compound is 2-methyl-4-(5-methylthio-1,3,4-thiadiazol-2-yl)-1,2,4triazolidin-3-one.

7. The herbicidal composition of claim 1 wherein the compound is 2-n-butyl-4-(5-methylsulfonyl-1,3,4-thiadiazol-2-yl)-1,2,4-triazolidin-3-one.

8. The herbicidal composition of claim 1 wherein the compound is 2-n-hexyl-4-(5-methylsulfinyl-1,3,4-thiadiazol-2-yl)-1,2,4-triazolidin-3-one.

9. A method of controlling weeds which comprises contacting the weeds with a herbicidal composition of claim 1.

* * * * *